United States Patent
Benner et al.

(10) Patent No.: US 10,449,394 B2
(45) Date of Patent: Oct. 22, 2019

(54) METHOD AND DEVICE FOR EFFICIENTLY IRRADIATING A TARGET FROM MULTIPLE IRRADIATION ANGLES IN A PARTICLE THERAPY SYSTEM

(71) Applicants: Varian Medical Systems Particle The4rapy GmbH., Troisdorf (DE); Varian Medical Systems, Inc., Palo Alto, CA (US)

(72) Inventors: Anke Benner, Roesrath (DE); Julie Clift, San Jose, CA (US); Andreas Hensel, Bergisch Glashack (DE); Richard Kane, Los Altos, CA (US); Jan Karis, Overath (DE); Nilesh Sinha, Fremont, CA (US); Brian Spatola, Huntington Beach, CA (US); Jan Timmer, Milpitas, CA (US)

(73) Assignees: Varian Medical Systems, Inc., Palo Alto, CA (US); Varian Medical Systems Particle Therapy GMBH, Troisdorf (DE)

( * ) Notice: Subject to any disclaimer, the term of this patent is extended or adjusted under 35 U.S.C. 154(b) by 0 days.

(21) Appl. No.: 15/707,838

(22) Filed: Sep. 18, 2017

(65) Prior Publication Data
US 2018/0064959 A1 Mar. 8, 2018

Related U.S. Application Data

(63) Continuation of application No. 14/866,280, filed on Sep. 25, 2015, now Pat. No. 9,764,163.

(51) Int. Cl.
*A61N 5/10* (2006.01)

(52) U.S. Cl.
CPC .......... *A61N 5/1081* (2013.01); *A61N 5/1049* (2013.01); *A61N 5/1082* (2013.01); *A61N 5/1079* (2013.01); *A61N 2005/1074* (2013.01); *A61N 2005/1087* (2013.01)

(58) Field of Classification Search
USPC ....................................... 250/492.3
See application file for complete search history.

(56) References Cited

U.S. PATENT DOCUMENTS

| | | |
|---|---|---|
| 7,835,492 B1 | 11/2010 | Sahadevan |
| 2003/0191384 A1 | 10/2003 | Svatos et al. |
| 2011/0049377 A1* | 3/2011 | Morf ................ A61N 5/1048 250/370.14 |
| 2011/0073778 A1 | 3/2011 | Natori et al. |
| 2011/0107270 A1 | 5/2011 | Wang et al. |
| 2012/0061582 A1 | 3/2012 | Iwata |

(Continued)

*Primary Examiner* — Kiet T Nguyen

(57) ABSTRACT

A control system is described which provides a user interface that displays a clear graphical representation of relevant data for a particle radiation therapy system (such as a pencil-beam proton therapy system) for treating multiple beam fields as efficiently as possible. The user interface allows a user to visualize a treatment session, select one or multiple beam fields to include in one or more beam applications, and dissociate beam fields previously grouped if necessary. Further embodiments extend the ability to initiate the application of the generated proton therapy beam and the grouping of beam fields to be performed remotely from the treatment room itself, and even automatically, reducing the need for manual interventions to setup between fields.

16 Claims, 7 Drawing Sheets

(56) References Cited

U.S. PATENT DOCUMENTS

2013/0086500 A1    4/2013   Kane et al.
2013/0235969 A1    9/2013   Winter et al.
2015/0231411 A1    8/2015   O'Neal, III et al.

* cited by examiner

100

METHOD AND DEVICE FOR EFFICIENTLY IRRADIATING A TARGET FROM MULTIPLE IRRADIATION ANGLES IN A PARTICLE THERAPY SYSTEM

This application is a continuation of U.S. application Ser. No. 14/866,280, now U.S. Pat. No. 9,764,163, filed Sep. 25, 2015, which is incorporated herein by reference in its entirety.

TECHNICAL BACKGROUND

Proton therapy is a type of external beam radiation therapy that is characterized by the use of a beam of protons to irradiate diseased tissue. The chief advantage of proton therapy over other conventional therapies such as X-ray or neutron radiation therapies is the ability to administer treatment dosages three-dimensionally by specifying the depth (i.e., limiting the penetration) of applied radiation, thereby limiting the inadvertent exposure of non-target cells to the potentially harmful radiation. This enables proton therapy treatments to more precisely localize the radiation dosage relative to other types of external beam radiotherapy. During proton therapy treatment, a particle accelerator—such as a cyclotron—is used to generate a beam of protons from, for example, an internal ion source located in the center of the cyclotron. The protons in the beam are accelerated (via a generated electric field), and the beam of accelerated protons is subsequently "extracted" and magnetically directed through a series of interconnecting tubes (called the beamline), often through multiple chambers, rooms, or even floors of a building, before finally being applied through a proton therapy device to a target area/subject in a treatment room.

Clinical institutions that provide proton beam therapy services require systems supporting efficient treatment workflows. This need is common to both clinics with standalone treatment suites having a dedicated cyclotron, and also to facilities with multiple treatment rooms that must share the beam from one cyclotron. Proton treatments are typically delivered as a series of discrete treatment fields, wherein the patient is setup and positioned for delivery of the proton beam to each field in a sequence of beam deliveries, one field at a time. These setups can require manual manipulations in the treatment room, manual preparations at the treatment console, or both, with time consumed between each treatment field for manual processes. For either single-room or shared-beam facilities, extra time consumed by manual field setups can unnecessarily lengthen treatment sessions, and that can negatively affect patient comfort. By enabling treatment fields to be grouped as a set of fields for automated treatment, manual setups between each field and the time to perform them may be concomitantly reduced. For shared-beam facilities, field groupings can also serve as an input to beam request functionality, if needed, such that a request could be for a grouped set of fields to be treated to completion.

Generally speaking, cyclotrons generate a proton beam at a fixed energy for the duration of a proton therapy treatment. During typical proton radiation treatments however, irradiating a tumor often requires irradiating an entire volume (a tumor, for example) at different depths within a patient or treatment subject. These depths, which may be referred to in discrete units as layers, naturally correspond to different "optimal" energy levels. Since cyclotrons operate only at a fixed energy during a treatment session, irradiating different depths can become problematic. Conventional methods for irradiating a volume are performed by applying a treatment beam and begin by targeting the furthest depth within a patient or subject. To achieve precise targeting and for differing depths, attenuating components are placed in the path of the proton beam at or near the point of emission to reduce the energy of the proton beam.

These components may include collimators and jaws that block portions of the beam from reaching untargeted regions in the subject, or filters and degraders that reduce the speed of the particles (and thereby the beam energy). However, when a treatment plan for a patient or treatment subject has multiple beam fields with different iso-centers (treatment targets), a technician or radiation therapist may need to enter the treatment area to add, modify, or remove the attenuating components to achieve the desired energy and positioning. For multiple beam fields, this can cause significant delays and additional discomfort for the treatment subject.

Moreover, due to the complexity of the underlying machines, their operating and maintenance procedures, and the gravity of the corresponding medical procedures, highly trained and skilled operators are needed to perform the calculations and actions necessary to make adjustments to a proton therapy device to achieve the desired beam energy and position levels. Naturally, this can result in further inefficiency, delays or even potential hazards

SUMMARY

This Summary is provided to introduce a selection of concepts in a simplified form that is further described below in the Detailed Description. This Summary is not intended to identify key features or essential features of the claimed subject matter, nor is it intended to be used to limit the scope of the claimed subject matter.

To overcome the difficulties inherent in conventional proton therapy systems, new techniques for automating, organizing, and graphically visualizing these procedures are herein provided. A control system is described which provides a user interface that displays a clear graphical representation of relevant data for a proton therapy system for treating multiple beam fields as efficiently as possible. The user interface allows a user to visualize a treatment session, select one or multiple beam fields to include in one or more beam applications, and dissociate beam fields previously grouped if necessary.

Further embodiments extend the ability to initiate the application of the generated proton therapy beam and the grouping of beam fields to be performed remotely from the treatment room itself, and even automatically, reducing the need for operator or physician to intervene to manually setup every individual treatment field. Additional information, such as the progress of a treatment session for which the beam is currently in use, is also clearly and intuitively visualized in a display device remotely displaced from the treatment room or area.

According to a second aspect of the invention, a method for displaying and receiving information corresponding to associating and disassociating beam fields in a graphical user interface is described. Proton beam delivery to treatment fields are automated according to the arrangement of the beam fields, thereby reducing the time a practitioner or therapist requires to prepare a patient or target treatment area between treatment fields.

By utilizing the systems and methods described above, a user is able to intuitively and efficiently perform the requisite functions to group multiple beam fields for automatic proton beam delivery to a treatment room in either a dedicated or shared beam facility. These functions—all of which can be performed within a single, integrated user-interface remotely from a treatment room—include a graphical environment for the arrangement of beam fields for one or more beam applications of a treatment session, or dissociation of previously associated beam fields. In a shared-beam proton therapy system, the grouping function can work in conjunction with a capable beam queuing and allocating function, wherein a grouping can also serve as one basis for forming a proton beam request with duration sufficient to permit treatment of the set of fields to completion.

BRIEF DESCRIPTION OF DRAWINGS

The accompanying drawings, which are incorporated in and form a part of this specification, illustrate embodiments of the disclosure and, together with the description, serve to explain the principles of the presently claimed subject matter:

DETAILED DESCRIPTION

Figure 1:
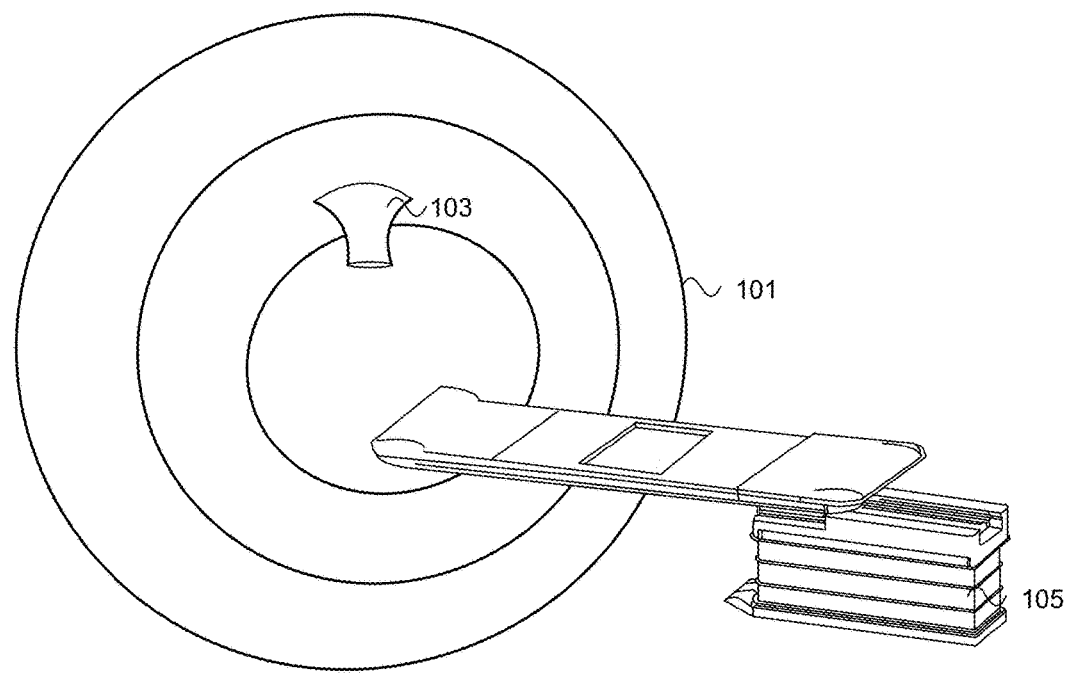
FIG. 1 depicts an exemplary proton therapy device in accordance with embodiments of the present disclosure.

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known processes, procedures, components, and circuits have not been described in detail as not to unnecessarily obscure aspects and features of the subject matter.

Portions of the detailed description that follow are presented and discussed in terms of a process. Although operations and sequencing thereof are disclosed in a figure herein (e.g., FIG. 2) describing the operations of this process, such operations and sequencing are exemplary. Embodiments are well suited to performing various other operations or variations of the operations recited in the flowchart of the figure herein, and in a sequence other than that depicted and described herein.

Some portions of the detailed description are presented in terms of procedures, operations, logic blocks, processing, and other symbolic representations of operations on data bits that can be performed on computer memory. These descriptions and representations are the means used by those skilled in the data processing arts to most effectively convey the substance of their work to others skilled in the art. A procedure, computer-executed operation, logic block, process, etc., is here, and generally, conceived to be a self-consistent sequence of operations or instructions leading to a desired result. The operations are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout, discussions utilizing terms such as "accessing," "writing," "including," "storing," "transmitting," "traversing," "associating," "identifying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

While the following example configurations are shown as incorporating specific, enumerated features and elements, it is understood that such depiction is exemplary. Accordingly, embodiments are well suited to applications involving different, additional, or fewer elements, features, or arrangements.

The claimed subject matter is directed to a particle beam control system which includes beam field grouping techniques within a clear, graphical user interface. In an embodiment, the beam control system may be implemented in conjunction with one or more instances of an integrated beam control panel or display, executed as computer-implemented graphical interfaces associated with one or more treatment rooms. Alternately, the beam control system may also be implemented as a single, dedicated beam control panel and graphical interface, such as when a cyclotron is dedicated to a single treatment room and not shared between multiple treatment rooms. The beam control system as described may be configured as a distributed system to provide customized graphical visualizations of a treatment session that includes one or more beam fields arranged for one or more beam applications, and integrated displays and control for a delivery of the beam for single or grouped beam fields to a beam control system.

According to further embodiments, the beam control system (through the beam control display, for example) may also graphically present beam status information for beam applications submitted by a user, such as the beam field delivery order of the grouped fields. In addition, the beam control interface may also provide controls for the user to add or remove beam fields to and from a beam field grouping. According to some embodiments, the display contents and controls indicate beam field grouping functions and treatment statuses via graphical or numeric means. According, the display and integrated controls can be significantly, if not completely, language-independent.

According to one or more embodiments, control of beam delivery can be provided remotely with respect to both the source of the particle beam, as well as from the treatment room itself. As recited herein, a beam is defined as a proton therapy beam or other irradiated particle beam used for therapy treatment. Each session may itself contain one or more treatment (beam) fields—the areas targeted by a beam during a portion or entirety of a treatment. These fields may be identified separately, collectively, or associated in one or more groups. In one or more embodiments, beam fields in the same group may be irradiated in a single, uninterrupted application. In one or more embodiments, beam fields may be grouped automatically based on beam field or treatment factors, such as treatment accessories, treatment table position, iso-centers, beam energy, and beam target locations. In one or more further embodiments, multiple requestors may each have grouped beam fields, wherein a shared beam may be applied to each grouping in turn, in accordance with a pre-defined queue.

As recited herein, a treatment facility is defined as a physical treatment complex consisting of multiple treatment suites. A treatment suite is defined as either a standalone treatment area, or one of multiple treatment areas within a facility where the beam can be used. Each treatment suite may consist of a treatment room, treatment control room, imaging alcove and various treatment preparation rooms.

As recited herein, a therapy team is described as one or more members of the group of therapists or proton therapy practitioners assigned to a given treatment suite for one or more treatment sessions. An (optional) beam requester is defined as a treatment suite team member that can potentially request the beam. Note that there may also be non-treatment requestors that can request to use the beam (e.g., research, maintenance, or service areas). These can also be beam requestors, or treatment suites. A beam application is defined herein as an application of the particle beam that is either waiting to be fulfilled or is presently being fulfilled. A beam sharing queue or beam queue is defined herein as an order in which beam requestors have requested the beam for a treatment session which have not been completed (but may include sessions currently in progress).

Exemplary Radiation Therapy Device

FIG. 1 depicts an exemplary radiation therapy device 100 in a treatment therapy room, in accordance with various embodiments of the claimed subject matter. As presented in FIG. 1, radiation therapy device 100 includes a gantry 101, a radiation treatment nozzle 103, and a patient positioner 105. In one or more embodiments, the gantry 101 may comprise an aperture through which at least a portion of the patient positioner 105 is able to enter (e.g., via automatic and/or mechanical means). In one or more embodiments, at least a portion of the gantry may be operable to rotate around the aperture (typically while at least a portion of the patient positioner is disposed within). For example, as depicted in FIG. 1, the gantry 101 may be implemented as a ring, at least a portion of which may be rotatable around an axis bisected by the patient positioner 105.

According to one or more embodiments, the gantry 101 is configured to receive irradiated particles through a beam line connected to a particle accelerator (not shown). The particle accelerator may be implemented as, but is not limited to, a proton accelerator such as a cyclotron or synchrotron. In one or more embodiments, the particle accelerator may be positioned remotely with respect to the treatment therapy room and may be shared between multiple radiation therapy devices housed in multiple treatment therapy rooms. Beam lines (e.g., vacuum sealed tubes or pipes used to transfer irradiated particles) are used to connect the particle accelerator to each of the radiation therapy devices. The irradiated particles are emitted from the radiation therapy device 100 through the treatment nozzle 103 located on the gantry 101. In one or more embodiments, the treatment nozzle 103 is rotated about the aperture of the gantry 101 through a rotation of at least a portion of the gantry. In alternate embodiments, movement of the treatment nozzle 103 may be performed via movement of one or more robotic appendages coupled to the gantry 101.

The treatment nozzle 103 may be configured to emit the irradiated particles in a spot scanning beam (also referred to as a "pencil beam"). In one or more embodiments, a spot scanning beam may be produced by crossing two or more beams at an extremely fine point, and a target area (beam field) may be irradiated with a raster scan (two-dimensional emission) of the spot scanning beam. In one or more embodiments, multiple beam fields sharing the same or proximate iso-centers may be irradiated with the spot scanning beam in a contiguous session, uninterrupted by application of the spot scanning beam to more distant or unrelated beam fields, for example. In further embodiments, beam fields that do not require the addition and/or removal of additional accessories such as (but not limited to) collimators, jaws, and range shifters, etc., may be irradiated in a contiguous beam application, as an automated treatment of a set of fields.

In one or more embodiments, the patient positioner 105 may include a table, chair, bench, or bed upon which a treatment subject may lie, sit, or rest upon. According to further embodiments, portions of the patient positioner 105 may be capable of movement, via automatic and/or mechanical means. For example, the incline of a portion of the resting surface may be increased or decreased (e.g., physically via a mechanism or automatically through a graphical user interface). Portions of the patient positioner 105 may also be equipped with means to rotate, extend, or retract. For example, according to one or more embodiments, a portion of the resting surface of the patient positioner 105 may be extended or physically positioned into an aperture of the gantry 101, such that a treatment subject resting on the patient positioner 105 bisects the plane at which the treatment nozzle 103 is directed.

According to one or more embodiments, one or both of the gantry 101 and the patient positioner 105 is/are capable of maneuvering, either independently or in conjunction, to align a treatment subject positioned on the patient positioner 105 with a treatment nozzle 103. Movement of the gantry 101 and/or patient positioner 105 may include, but is not limited to, rotation, extension, retraction, contraction, adduction, abduction, etc. of one or more articulated surfaces or portions of the gantry 101, and/or patient positioner 105. In one or more embodiments, treatment nozzle 103 may also be capable of limited movement, via multi-axial rotation, for example.

According to an embodiment, a treatment subject may be positioned (e.g., prone) on a patient positioner 105 at an initial or starting position. One or more portions of the patient positioner 105 may extend towards an aperture presented by the gantry 101, such that a target region of the treatment subject is aligned with a position of the treatment nozzle 103, located on or around an inner surface of the gantry 101. In alternate or further embodiments, the gantry 101 may also rotate in an arc around the circumference of the gantry 101 to more closely align the treatment nozzle 103 to produce the desired beam field. Once the gantry 101, treatment nozzle 103, and/or patient positioner 105 are aligned in the desired orientation, treatment therapy may begin. Specifically, an iso-center in the treatment subject may be aligned with the treatment nozzle 103 via movement of the gantry 101 and/or patient positioner 105. In one or more embodiments, treatment therapy may comprise the application of irradiated particles generated at a (remote) particle accelerator, received in the gantry 101, and emitted (e.g., as a raster scan) in a beam field from the treatment nozzle 103 at an iso-center located in a treatment subject according to a pre-determined treatment therapy plan.

In one or more embodiments, one or more of the treatment nozzle 103, gantry 101, and/or patient positioner 105 may maneuver or be maneuvered to achieve a more ideal alignment in between applications of beam fields. In one or more embodiments, beam fields with the same or substantially identical iso-centers in the treatment subject may be applied as a contiguous session, as an automated treatment of some or all fields in a session. Movement of the gantry 101, treatment nozzle 103, and/or patient positioner 105 may be performed automatically, via pre-programmed instructions that correspond to optimized alignments for desired iso-centers, or may be controlled remotely via a user interface.

Automatic Multi-Field Grouping

Figure 2:
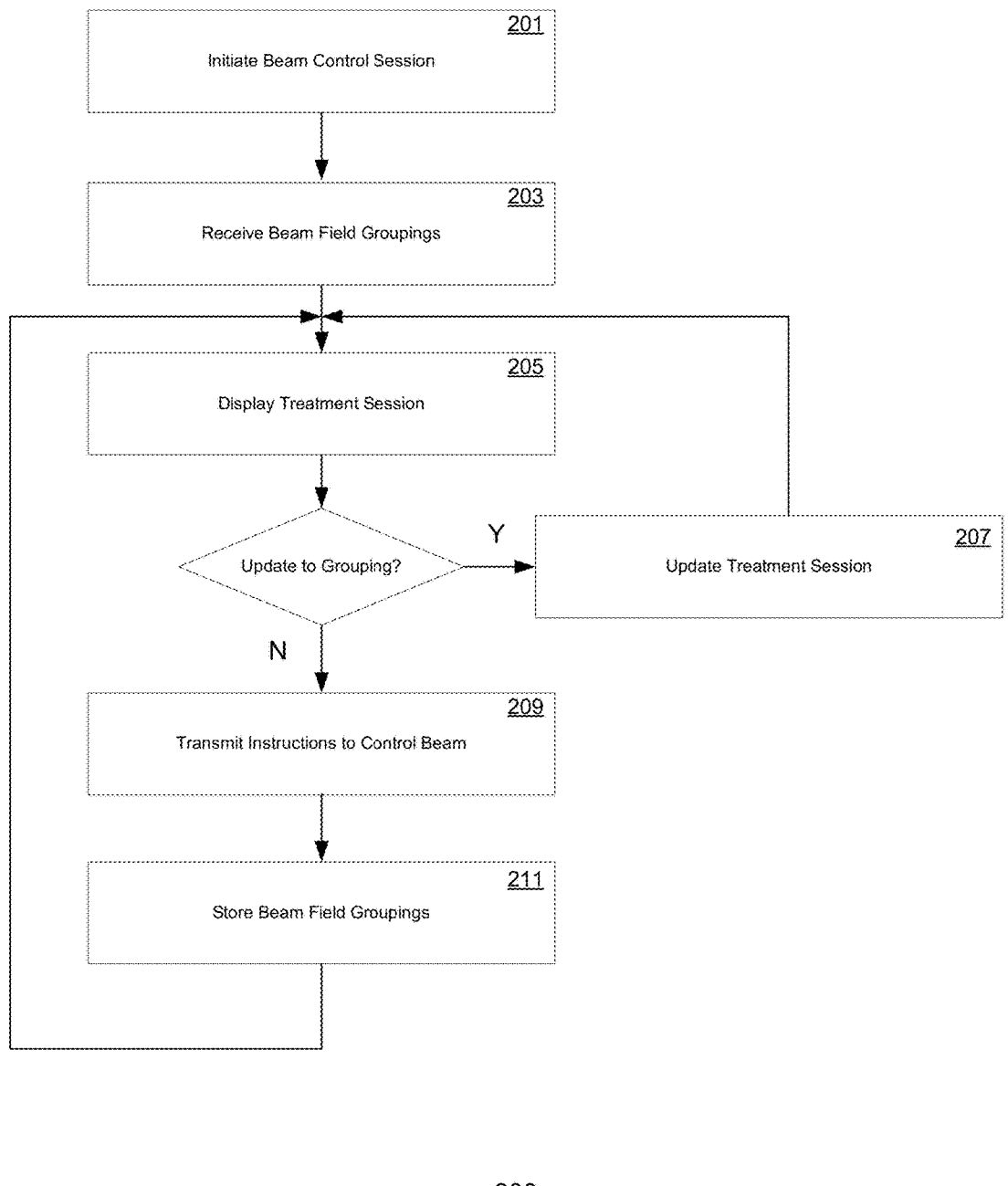
FIG. 2 depicts a flowchart of a process for providing beam field arrangement functionality in an integrated control panel, in accordance with embodiments of the present disclosure.

FIG. 2 depicts a flow chart 200 of a process for requesting a treatment that may include multiple grouped fields in a single beam request for a shared therapy beam. Steps 201-211 describe exemplary steps comprising the process 200 depicted in FIG. 2 in accordance with the various embodiments herein described. In one embodiment, the process 200 is implemented in whole or in part as computer-executable instructions stored in a computer-readable medium and executed in a computing device.

At step 201, a user-actuation in an integrated beam control panel is received as input. In one embodiment, the integrated beam control panel may be instantiated in a plurality of computing devices in a facility, such as a treatment facility implementing a shared particle beam system. The user-actuation may work in conjunction with, for example, a beam request user-interface of the integrated control panel to allocate the treatment beam for the duration sufficient to permit completion of treatment of a set of grouped fields.

According to an aspect of the claimed subject matter, whether for a treatment suited with a dedicated beam, or a shared-beam, a user can perform a user-actuation which results in the treatment beam being available for a duration sufficient to permit completion of treatment of all of the grouped fields.

According to further embodiments, the session area which displays treatment fields permits selecting a scope of the treatment fields that the beam will be used for upon its activation. The scope of the treatment may include, for example, a single field, or a grouping of associated fields. These fields correspond to one or more treatment fields in a treatment session, as pre-defined by a treatment plan for a patient of proton therapy treatment, for example. At step 203, a user input is received indicative of a grouping of two or more beam fields. In one or more embodiments, this scoping can cooperate with a beam request user-interface which may also include functionality to allow a user to select multiple beam fields to be associated within a treatment session for a submitted request. Association may be elected as a binary toggle that corresponds to a first selected beam field (e.g., with or without association with the first selected beam field), or multiple beam fields may be selected within the user interface during step 203 to be associated. A user may group beam fields based on the patient or target of the beam. For example, beam fields of higher priority for a patient based on the treatment plan of the patient may be grouped together. Other factors that may be considered when multiple beam fields are grouped together include, but are not limited to: shared beam accessories, treatment table position, the patient's (dis)comfort, treatment plan requirements, and estimated beam field treatment durations, gantry position and/or angle, etc.

Once elected by the user in step 203, beam fields are associated in the control system of the shared therapy beam and verified for compatibility. According to one or more embodiments, beam fields that share the same (or substantially similar) iso-centers and/or energy may be grouped together, either automatically or by the user via user input received through the user interface, and beam requests may be fulfilled for beam fields that are grouped together as a single contiguous session, and which also do not require further adjustment of beam accessories. For example, if the addition, modification, or removal of one or more beam accessories is required between two beam fields, the system may disallow grouping of the two beam fields in a contiguous beam application. That is, a beam request for a grouping of beam fields may be fulfilled such that every beam field in the beam field grouping is treated without interruption, e.g., via a diversion and re-allocation of the generated proton beam to other treatment rooms and/or other unassociated beam fields in the same treatment room. In one or more embodiments, the grouping of multiple fields in step 203 and the association in the system may be performed prior to the submission of a beam request performed in step 201, or during the submission process. According to further embodiments, a pre-submitted request may be updated with grouping(s) of multiple fields performed in step 203 via user input received post submission.

At step 205, the beam display is updated to reflect the modification to the beam field grouping. The beam display may include, for example the scope of any beam field grouping (e.g., single, multiple, or group fields).

In one or more embodiments, the beam display may be customized for the user by specifically identifying (e.g., emphasizing) the position of one or more beam fields relative to other beam fields for the user's current treatment session. The identification may consist of visually distinguishing the graphical representation of each beam field comprising the user's treatment session, by size, color, form, or other visual indicia. Accordingly, each beam display and/or beam field grouping visualization may be customized to emphasize a different beam field grouping in the beam display.

For embodiments that include a shared beam source, the beam field grouping controller can convey field grouping information as needed to permit coordination with other system components. For example, the field grouping controller can communicate field groupings in making beam requests to a capable beam queuing and allocation function, so that those requests can be queued for beam allocation, and statuses reflected in beam queue displays.

According to one or more embodiments, beam field grouping may be performed for a beam request at any time until beam usage is granted for the beam request. A beam request may be updated with new or revised beam groupings, or a grouping may be removed. In one or more embodiments, grouped beam fields may also be revised to dissociate one or more beam fields from the existing group. The beam field grouping display is dynamically updated (at step 207) whenever a subsequent beam field grouping or a prior beam field grouping is added, modified, or removed, such as when a beam field grouping is canceled or disassociated.

In one or more embodiments, a beam control system executing along with the beam control panel verifies that the revised beam request complies with pre-established policies, and all grouped beam fields are compatible. For example, if adding a beam field to another beam field (thereby creating a grouping) or adding a beam field to an existing grouping would require the addition, modification, or removal of a beam accessory during a single beam application, the beam field grouping may be disallowed by the beam field controller. The beam control system may also verify that the beam fields share a treatment isocenter, or if positioning of the gantry and/or treatment subject would be required. The beam control system may also determine whether the user is authorized to make changes to the beam application (e.g., via a user authentication protocol). According to still further embodiments, the beam control system may also group fields to perform a "dry run" (a practice run) that mimics the actions and movement taken by the gantry, nozzle, and/or patient positioned—but does not include application of the particle beam—to ensure sufficient clearance between the therapy device and the treatment subject for each beam field of the beam field grouping. Once updated and verified in step 207, the process returns to step 205 to display the most current beam grouping configuration while awaiting further modifications to the beam groupings.

Finally, at step 209, application of the beam is effected based on the beam grouping order. For a beam field grouping, this may consist of a single, contiguous beam application for each of the beam fields comprising the grouping. Beam application may terminate (or pause) once the last beam field of a grouping is treated. Once the beam application is terminated, the beam and/or subject may be prepared for the next grouping of beam fields. For example, one or more of the treatment nozzle, patient positioner, and beam accessories may be modified (e.g., by a physician and/or beam operator) to comply with the next grouping of beam fields.

According to further embodiments, once a beam field grouping is verified, the grouping may be saved (e.g., stored in a memory device) in the beam control system at step 211. The grouping may be saved, for example, to correspond to the treatment subject, a treatment plan, a treatment session, or a combination thereof. In still further embodiments, multiple beam field groupings may be stored for a treatment session. Subsequent treatment sessions for the treatment subject that involved the same beam fields may be automatically initiated by referencing the stored beam field grouping. During subsequent treatment sessions, (i.e., treatment sessions that reference pre-grouped fields), the application of the beam according to grouped fields may be initiated without further user input and/or repeated beam field grouping. Under such implementations, the beam console or display may also include a user authorization system to establish and enforce appropriate user rights to set up and/or initiate an automated treatment, Exemplary Field Grouping Interface With reference now to FIGS. 3-5, example graphical user interfaces of the beam field grouping interfaces are herein described. In an embodiment, the beam field grouping interface displays a graphical depiction of one or more beam fields. The one or more beam fields may comprise, for example, the beam fields to be treated during a treatment session and according to a treatment plan. Alternately, the one or more beam fields may comprise a selection or all of the beam fields included in a beam request. According to one or more embodiments, beam field grouping interface 300 allows the user to specifically select multiple beam fields to be associated for one or more beam applications during a treatment session. For example, the user may be able to select with specificity whether a beam field is included or whether a beam application is for a single field (indicated as the single vertical bar) or multiple fields (multiple bars). The user can configure a treatment session by actuating on the single field or multiple field buttons with just a single user actuation (click).

Figure 3:
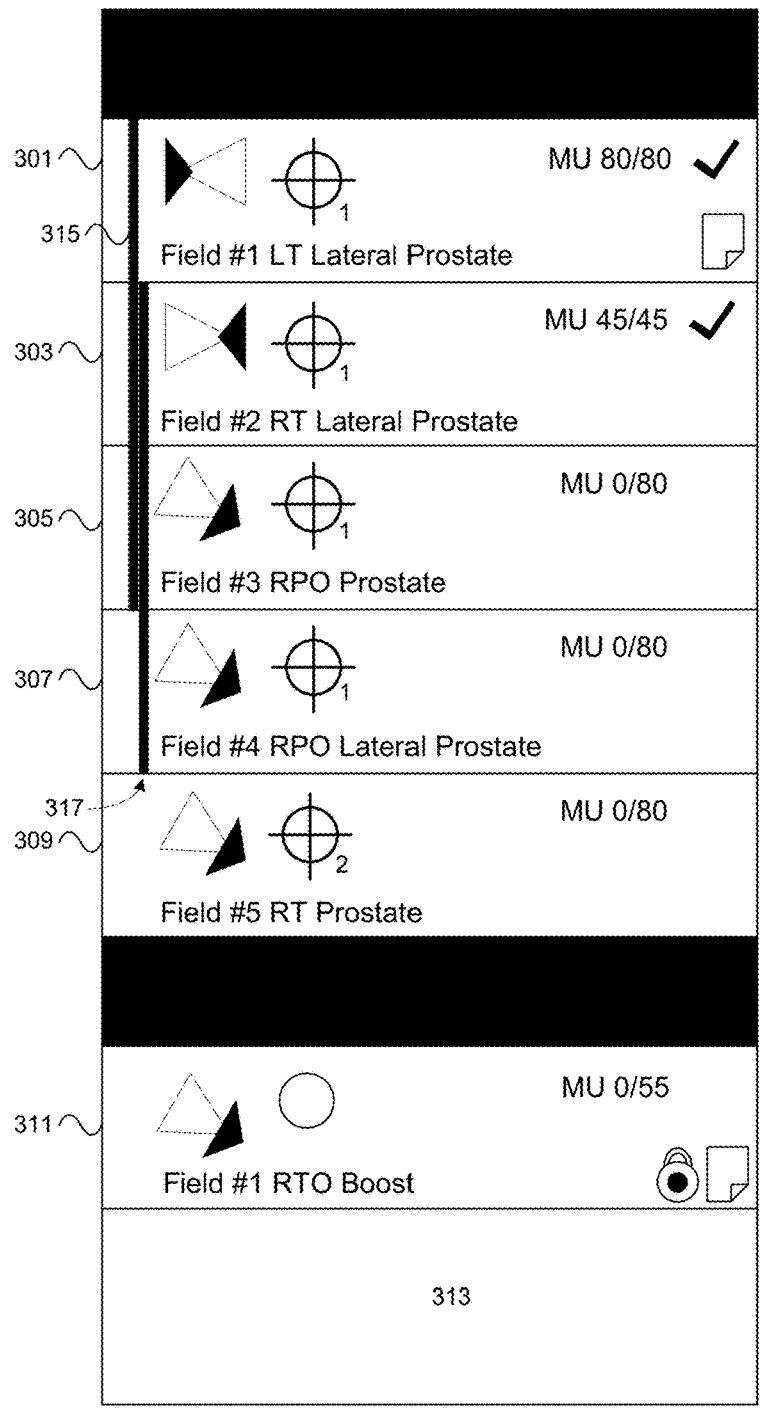
FIG. 3 depicts a first exemplary field grouping graphical interface, in accordance with embodiments of the present disclosure.

As presented in FIG. 3, exemplary beam field grouping interface 300 depicts a beam field grouping interface for a current treatment session that includes six beam fields (e.g., beam fields 301, 303, 305, 307, 309, and 311). Each beam field may include visual indicia regarding the beam field, such as: the position of the treatment nozzle and/or the angle of approach for the beam application to the iso-center; an identification of the beam field and/or isocenter; information regarding the beam itself, such as energy and/or dosage; and whether the beam field has been treated during the current session. One or more beam fields may be graphically represented as being grouped together. For example, as depicted in FIG. 3, bar 315 appears across beam fields 301, 303, and 305 to indicate that the beam fields belong to a single group. According to further embodiments, beam fields may belong to multiple groupings (e.g., indicated by bars 315 and 317). One or more beam fields which are not grouped (e.g., beam field 309) may be presented in user interface 300. As presented, ungrouped beam fields may be visually distinguished from beam fields belonging to the same group or association.

Beam field grouping interface 300 may also display treatment fields separated by beam applications, or by separate usage requests in shared-beam embodiments. For example, beam fields 301-309 may be included in a beam application (or beam request), whereas beam field 311 in the lower portion of user interface 300 may be part of the treatment session, but not part of the original beam request/beam application. Beam field grouping interface may also include a note panel 313 that displays additional information for one or more treatment fields. Treatment fields may indicate (via a graphical icon) additional information that may be of interest to the treatment provider (e.g., radiation therapist or technician). This information may include particular details regarding the treatment subject that may be relevant during the application of the beam for that beam field and/or aggregated from the beam fields comprising the beam field grouping.

According to one or more embodiments, each of the beam fields 301, 303, 305, 307, 309, and 311 may be implemented as user-input buttons configured to respond to user-actuations to perform designated functions and/or display information, and to allow one-action beam field grouping. As presented in user interface 300 for example, the user may group multiple beam fields together by actuating the beam field buttons. An actuation on a beam field may be visually confirmed, by the extension of bar 315 through some or all of the beam field, for example. Actuating the button of a beam field again may ungroup the beam field from one or more of its current groupings.

Figure 4:
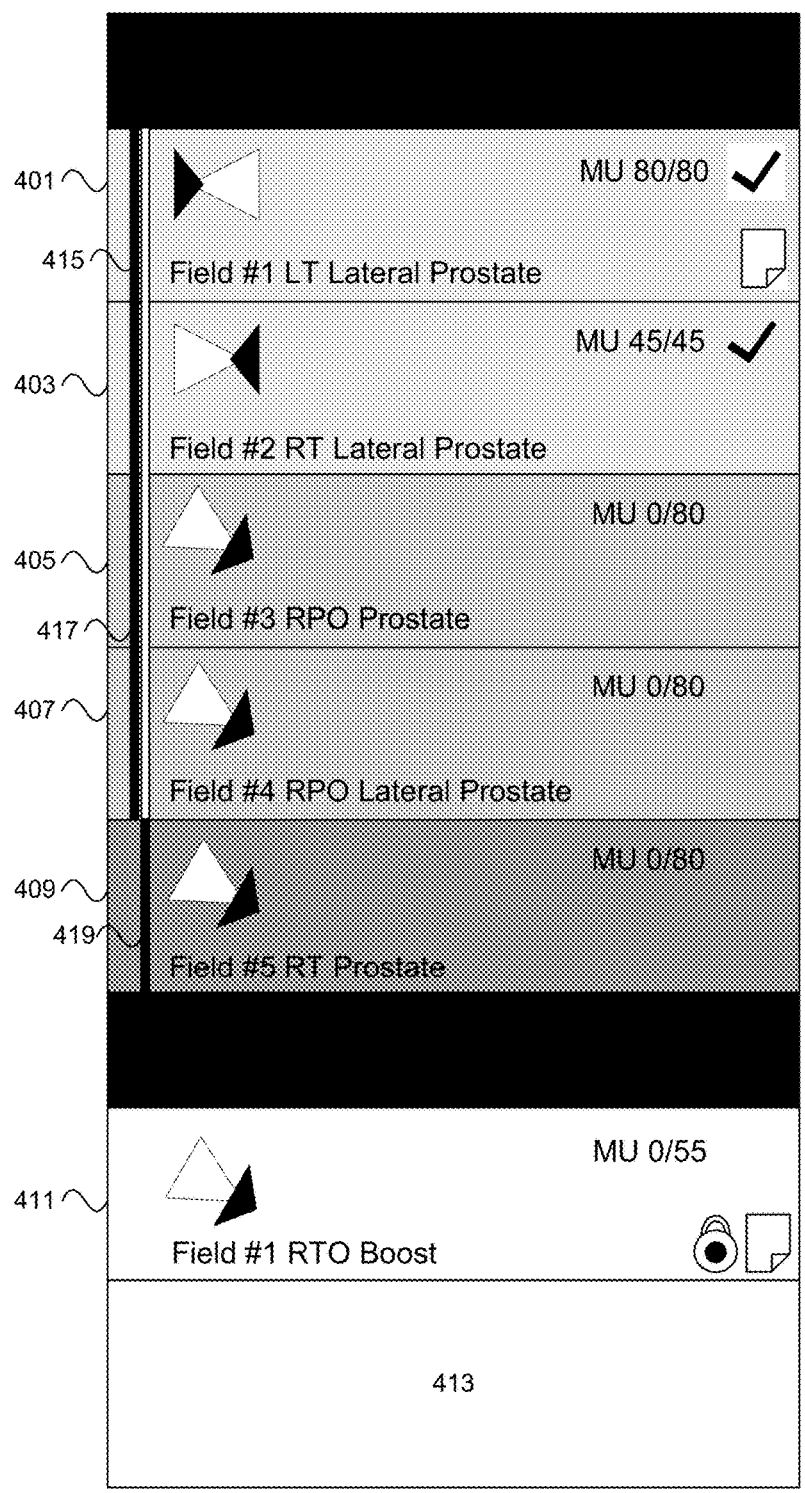
FIG. 4 depicts a second exemplary field grouping graphical interface, in accordance with embodiments of the present disclosure.

User actuation may be graphically acknowledged in the panel 300 by changing the appearance of the icon of the field actuated. FIG. 4 depicts such an exemplary beam field grouping interface 400. As depicted in FIG. 4, the graphic representations of the beam fields may be different, based on the current status of the beam field (e.g., whether treatment for the beam field has been completed, is currently in progress, or still pending), and/or the inclusion or exclusion of the beam field for a grouping. For example, beam fields 401 and 403 of FIG. 4 may share the same color in a graphical user interface, which may indicate the completion of treatment for those beam fields. Beam fields 405 and 407 may also share a color (not shown) that is readily distinguishable from beam fields 401 and 403, indicating that treatment for those beam fields is underway. Beam field 409 is represented with yet another color that indicates the beam treatment for the beam field is still pending. Grouping for beam fields 401-409 may also be indicated via color, and/or via bars 415, 417, and 419. As with FIG. 3, beam fields included in the treatment plan but belonging to a different treatment session or separate group may also be represented (e.g., as beam field 411) in beam field grouping interfaces 400 and 500, along with a field (413) to display notes, or other pertinent information.

Figure 5:
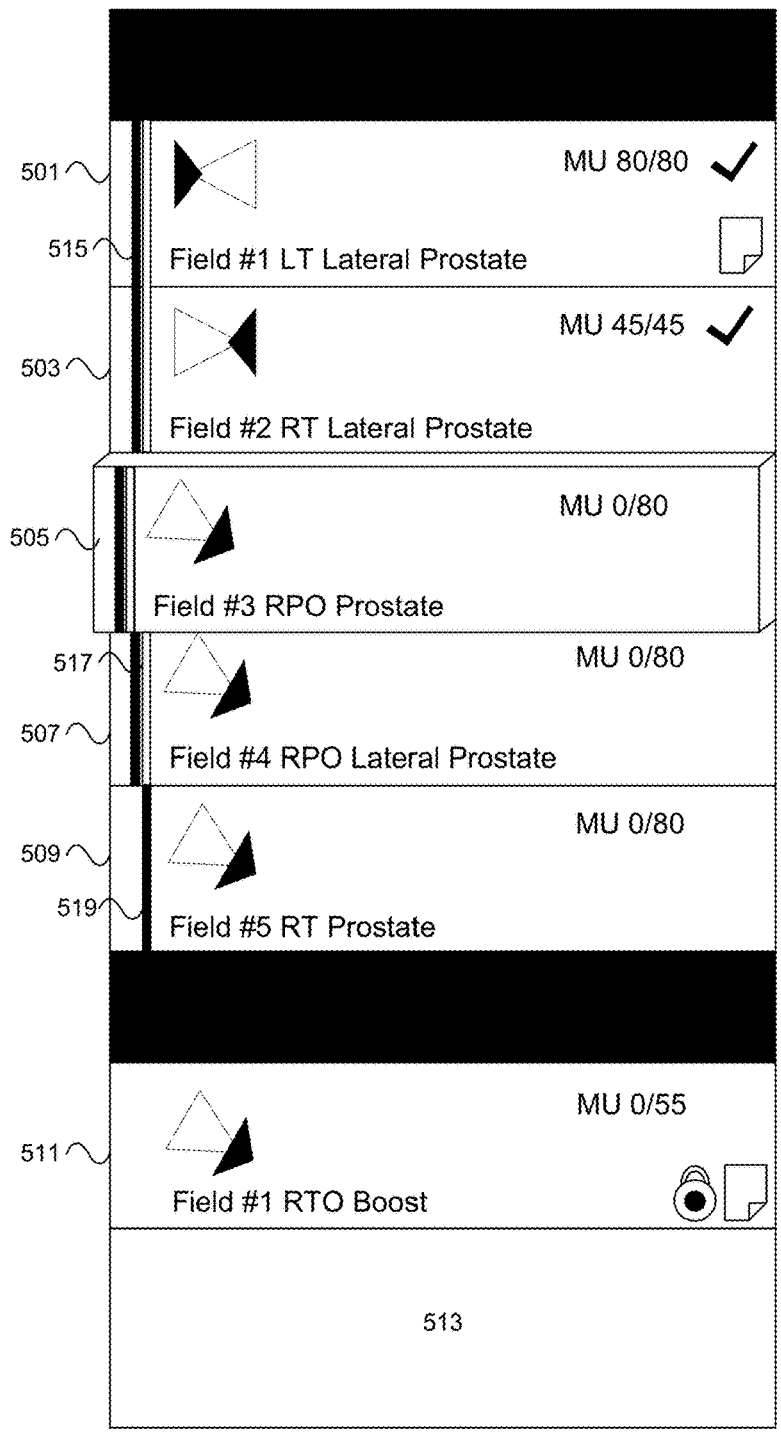
FIG. 5 depicts a third exemplary field grouping graphical interface, in accordance with embodiments of the present disclosure.

Other visual indicia may be used to convey association or actuation. For example, the colors of the selected icon may be reversed, or the size of the icon may be modified, etc. FIG. 5 depicts such an exemplary beam field grouping interface 500. As depicted in FIG. 5, the graphic representations of the beam fields of an actuated beam field is represented by a graphical displacement of the actuated beam field from its normal or typical position. As presented, beam field 505 appears to be slightly displaced (along a third dimension) from the remaining beam fields (e.g., beam fields 501, 503, 507, and 509) in the group of beam fields presented in user interface 500. Actuation of beam field 505 (via a user input device for example) may be performed to associate beam field 505 with an existing group, or to disassociate beam field 505 from a previously associated group. As with FIG. 3, beam fields included in the treatment plan but belonging to a different treatment application or separate group may also be represented (e.g., as beam field 511) in beam field grouping interfaces 400 and 500, along with a field (513) to display notes, or other pertinent information.

Once a beam field grouping is added or updated, the beam field may be submitted to the beam control system. Submission may be performed automatically (e.g., periodically), or via user actuation of a submission or "save" button on the beam field grouping interface.

Figure 6:
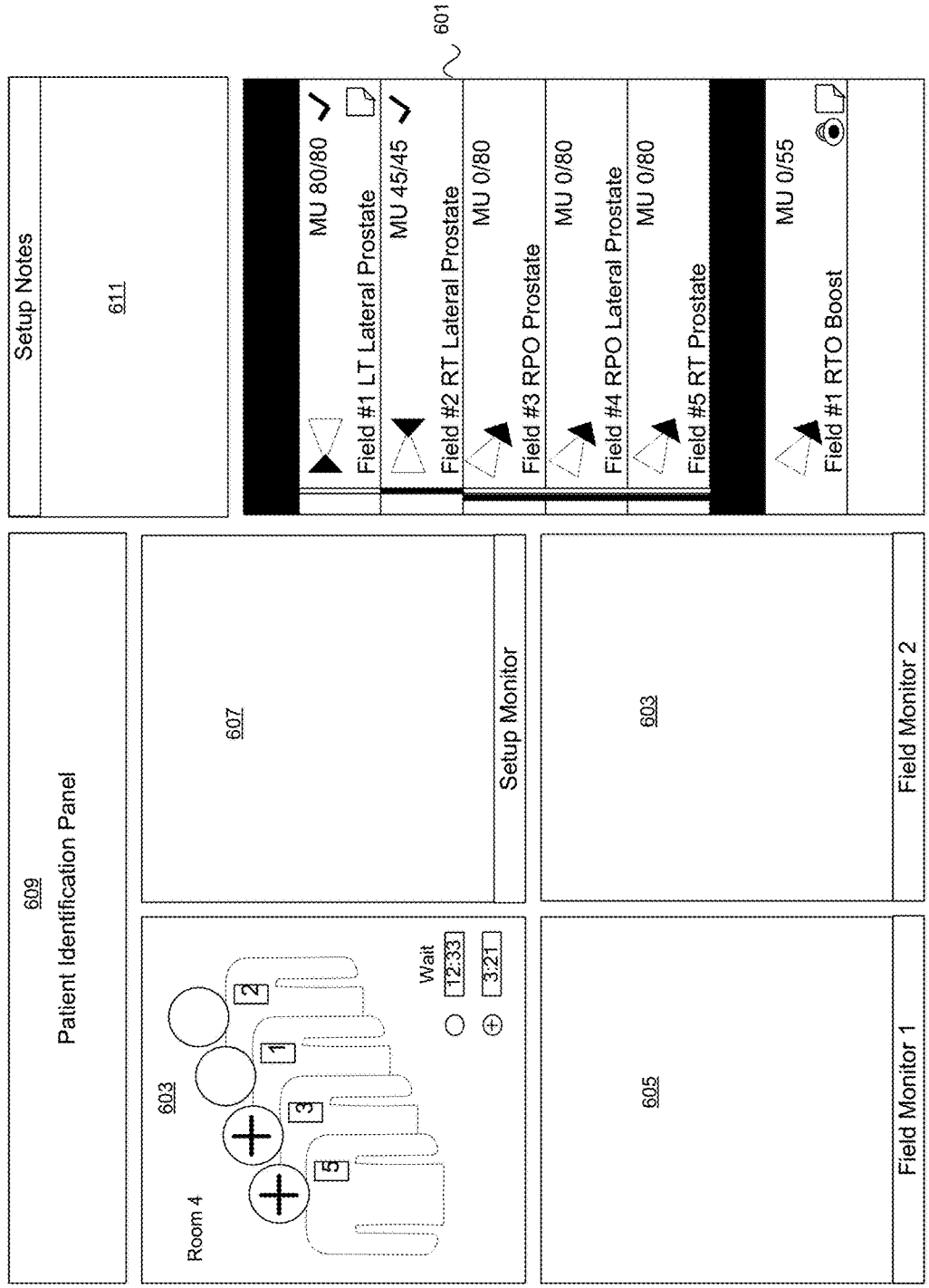
FIG. 6 depicts an exemplary graphical user interface for beam field grouping, in accordance with embodiments of the present disclosure.

FIG. 6 depicts an example display of an in-room monitor comprised in an integrated beam control panel 600. According to one or more embodiments, user interface 600 may be presented in the integrated beam control panel separately, or as one of a plurality of panels presented during or in anticipation of preparing a patient or subject to receive treatment from a shared beam. FIG. 6 depicts such an embodiment—wherein a beam field grouping interface 601 is one panel of a composite of multiple panels displayed during the preparation period for a patient. As depicted in FIG. 6, other display elements useful to prepare a patient or subject for beam application may be shown. These other display elements provided by the beam sharing panel may include an identification panel 609 corresponding to the current treatment being administered, such as the treatment room, therapist, patient, treatment session, etc. for which the beam request is to be fulfilled.

In one or more embodiments, the treatment system may also be equipped with position verification capabilities. These capabilities may be implemented in, for example, the imaging system, a motion management system and/or a treatment console verification system to automatically verify patient position during and/or in preparation for each of the grouped fields in sequence as each field is encountered. The position verification may, if necessary, automatically reposition the patient and/or patient positioner if necessary prior to an application of the beam to the beam field grouping. According to further embodiments, the position verification capabilities may also incorporate features to allow the user or operator to verify a system suggested position change before accepting, rejecting, or otherwise modifying the suggested change in position.

Further display elements may include in-room monitoring of a patient (e.g., the patient's position). As depicted in FIG. 6, a beam queue 601 (for shared beam embodiments), a set-up monitor (monitor display 603) and one or more field monitors 1 and 2 (monitor display 605, 607) are presented to verify patient preparation and procedures, such as positioning the patient properly and with the proper treatment accessories and immobilization devices. An additional panel (setup notes panel 611) can list assorted preparation notes that the beam requestor (e.g., radiologist, oncologist, etc.) may refer to in order to prepare the patient for beam delivery.

Alternatively, the panel may be integrated and adapted for use with any therapy setting with a shared or finite therapeutic resource, and where more than one potential consumer of the resource can request a usage of the shared resource. Additionally, the display panel may be integrated and adapted for use with any resource sharing situation where a resource requestor can self-request and group multiple fields for an operation to be performed for the associated fields in a single, contiguous session. According to one or more embodiments, usage of the resource may be granted to other requesting users in between grouped beam fields. Still further embodiments can provide privacy benefits such as anonymous or proxy identities for public displays. Alternatively, other requesting users may have identities masked.

Exemplary Computer System

Figure 7:
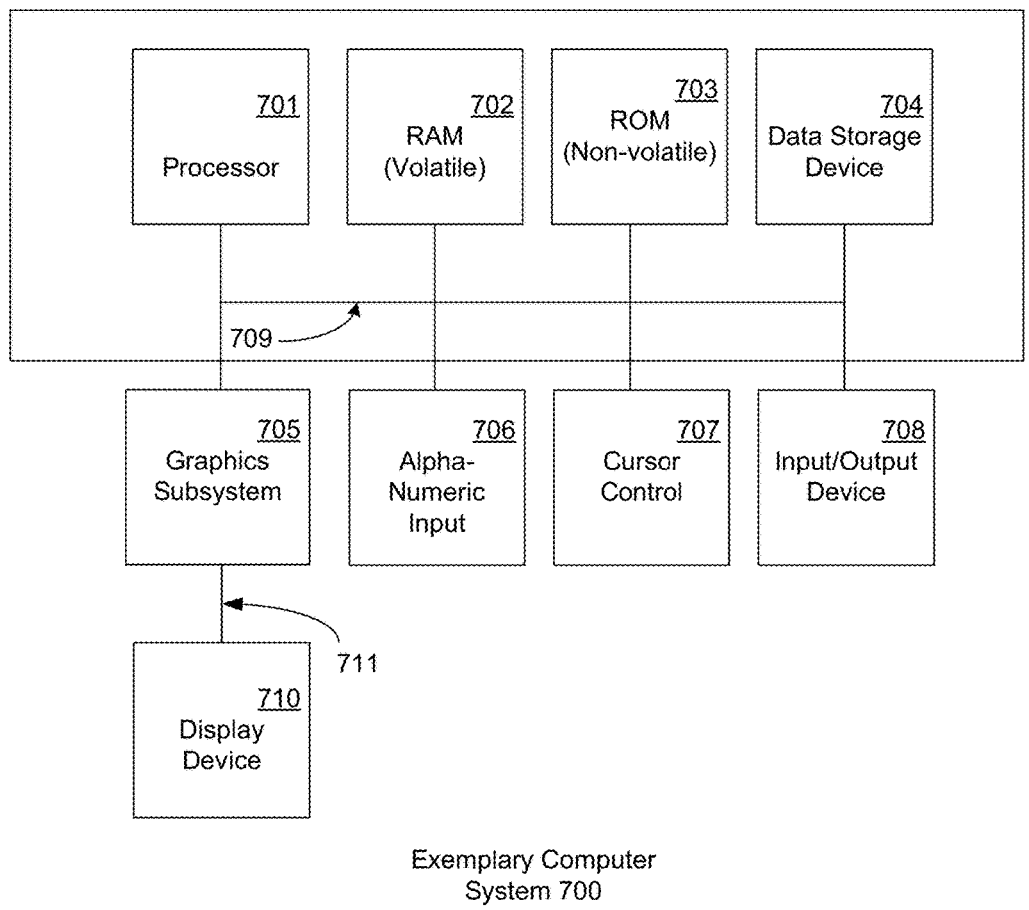
FIG. 7 depicts an exemplary computing environment, in accordance with embodiments of the present disclosure.

As presented in FIG. 7, an exemplary system 700 upon which embodiments of the present invention may be implemented includes a general purpose computing system environment. In its most basic configuration, computing system 700 typically includes at least one processing unit 701 and memory, and an address/data bus 709 (or other interface) for communicating information. Depending on the exact configuration and type of computing system environment, memory may be volatile (such as RAM 702), non-volatile (such as ROM 703, flash memory, etc.) or some combination of the two.

The computer system 700 may also comprise an optional graphics subsystem 705 for presenting information to the radiologist or other user, e.g., by displaying information on an attached display device 710, connected by a video cable 711. According to embodiments of the present claimed invention, the graphics subsystem 705 may be coupled directly to the display device 710 through the video cable 711. A graphical user interface of an application for grouping multiple beam fields may be generated in the graphics subsystem 705, for example, and displayed to the user in the display device 710. In alternate embodiments, display device 710 may be integrated into the computing system (e.g., a laptop or netbook display panel) and will not require a video cable 711.

Additionally, computing system 700 may also have additional features/functionality. For example, computing system 700 may also include additional storage (removable and/or non-removable) including, but not limited to, magnetic or optical disks or tape. Computer storage media includes volatile and nonvolatile, removable and non-removable media implemented in any method or technology for storage of information such as computer readable instructions, data structures, program modules or other data. RAM 702, ROM 703, and external data storage device (not shown) are all examples of computer storage media.

Computer system 700 also comprises an optional alphanumeric input device 706, an optional cursor control or directing device 707, and one or more signal communication interfaces (input/output devices, e.g., a network interface card) 708. Optional alphanumeric input device 706 can communicate information and command selections to central processor 701. Optional cursor control or directing device 707 is coupled to bus 709 for communicating user input information and command selections to central processor 701. Signal communication interface (input/output device) 708, also coupled to bus 709, can be a serial port. Communication interface 708 may also include wireless communication mechanisms. Using communication interface 708, computer system 700 can be communicatively coupled to other computer systems over a communication network such as the Internet or an intranet (e.g., a local area network).

The integrated beam control panel 600 described above with respect to FIG. 6 may be executed in a computing device, such as computing system 700, for example. In one or more embodiments, computing system 700 may be located in the same treatment room or suite as the treatment device 100 described above with respect to FIG. 1. Alternately, computing system 700 may also be located externally with respect to the treatment room or suite containing treatment device 100, so that the operator or technician is not required to be in the same room or suite as the treatment subject when the treatment is administered. For embodiments where beam fields with the same iso-centers are grouped together, the operator of the treatment device may initiate the application of the beam for multiple beam fields without having to enter the treatment suite and manually adjusting the gantry or treatment nozzle (e.g., to add/remove/adjust the position of collimators), thereby saving considerable time and providing a more efficient allocation of the shared beam resource.

By utilizing the systems and methods described above, various critical functions for proton beam management in a dedicated or shared beam facility may be performed. These functions—all of which can be performed within a single, integrated user-interface—include functionality for grouping multiple fields together for a treatment session, visualization of the grouping and/or treatment session, dissociation of grouped fields, and in a shared-beam system, to communicate such grouping information to a beam queuing and allocation function for use for example, in making beam requests. As many (if not all) of these functions may be requested by the user through single actuations, a user is able to intuitively and efficiently perform these requisite functions for themselves, and even automatically for pre-stored beam groupings.

Although the subject matter has been described in language specific to structural features and/or process and/or logical acts, it is to be understood that the subject matter defined in the appended claims is not necessarily limited to the specific features or acts described above. Rather, the specific features and acts described above are disclosed as example forms of implementing the claims.

What is claimed is:

1. A particle therapy device comprising:
a gantry configured to receive a stream of particles;
a treatment nozzle coupled to the gantry and configured to emit the stream of particles as a beam at a plurality of iso-centers disposed in a target subject;
a computing system configured to automatically control an emission of the beam of particles to irradiate a plurality of beam fields corresponding to the plurality of iso-centers,
wherein the computing system is further configured to form a group comprising a subset of beam fields of the plurality of beam fields, wherein the beam fields in the group have a same characteristic, and wherein adding a beam field of the plurality of beam fields to the group is disallowed if the beam field would require changing an accessory of the beam during a contiguous application of the beam to the beam fields included in the group,
further wherein, the computing system is further configured to control the emission of the beam of particles to irradiate the group of beam fields in the contiguous application.

2. The particle therapy device of claim 1, wherein the gantry is configured to automatically rotate the treatment nozzle along a plurality of axes around the target subject.

3. The particle therapy device of claim 1, wherein the computing system is further configured to control a movement of the gantry around the target subject based on a position of the plurality of beam fields.

4. The particle therapy device of claim 1, wherein the computing system comprises:
a memory device comprising programmed instructions; and
a processor configured to execute the programmed instructions to implement a graphical user interface operable to display a graphical representation operable to remotely control a usage of the particle therapy device.

5. The particle therapy device of claim 4, wherein the graphical user interface is further operable to allow a user to submit a request for usage of the stream of particles to irradiate the group of beam fields contiguously, wherein the gantry automatically arcs around the target, and administers the beam as it does so, according to a treatment plan.

6. The particle therapy device of claim 4, wherein the programmed instructions further comprise instructions to detect and avoid impending collisions due to a movement of the treatment nozzle or target subject.

7. The particle therapy device of claim 4, wherein the programmed instructions further comprise instructions to establish and enforce appropriate user rights to set up an automated treatment.

8. The particle therapy device of claim 4, wherein the programmed instructions further comprise instructions to verify a position of a target subject.

9. The particle therapy device of claim 8, wherein the programmed instructions further comprise instructions to allow a user to verify a position change, and to automatically re-position the target subject in response to a user verification of the position change.

10. The particle therapy device of claim 4, wherein the programmed instructions further comprise instructions to:
generate a display in the graphical user interface of the plurality of beam fields;

receive a plurality of user actions through the graphical user interface, the user actions corresponding to a user-initiated grouping of the plurality of beam fields;

verify the group of the plurality of beam fields for compatibility;

create the group comprising the subset of beam fields; and store the group of beam fields in a memory device.

11. The particle therapy device of claim 10, wherein the programmed instructions further comprise instructions to receive user input corresponding to a programming of a plurality of motions corresponding to a movement of the treatment nozzle.

12. The particle therapy device of claim 10, wherein the programmed instructions further comprise instructions to receive, through the graphical user interface, a request to apply the beam to the group of beam fields contiguously.

13. The particle therapy device of claim 4, wherein the programmed instructions further comprise instructions to:

receive a user action through the graphical user interface, the user action corresponding to an ungrouping of the group of beam fields; and disassociate the group of beam fields into a plurality of discrete beam fields.

14. The particle therapy device of claim 1, wherein the same characteristic is selected from the group consisting of: the same iso-center; and the same energy.

15. The particle therapy device of claim 14, further comprising a subject positioning device configured to support and automatically position the target subject, wherein the subject positioning device is moved to position the target subject to align the iso-center with the treatment nozzle.

16. The particle therapy device of claim 1, wherein the accessory of the beam is selected from a group comprising: a collimator, a jaw, and a range shifter.

* * * * *

UNITED STATES PATENT AND TRADEMARK OFFICE
CERTIFICATE OF CORRECTION

| | | |
|---|---|---|
| PATENT NO. | : 10,449,394 B2 | Page 1 of 1 |
| APPLICATION NO. | : 15/707838 | |
| DATED | : October 22, 2019 | |
| INVENTOR(S) | : Anke Benner et al. | |

It is certified that error appears in the above-identified patent and that said Letters Patent is hereby corrected as shown below:

On the Title Page

Item [71], insert --Varian Medical Systems Particle Therapy GmbH., Troisdorf (DE); Varian Medical Systems, Inc., Palo Alto, CA (US)--

Signed and Sealed this
Twenty-eighth Day of January, 2020

Andrei Iancu
*Director of the United States Patent and Trademark Office*